US00PP15810P2

(12) United States Plant Patent
Olesen et al.

(10) Patent No.: US PP15,810 P2
(45) Date of Patent: Jun. 28, 2005

(54) FLORIBUNDA ROSE PLANT NAMED 'POULCS017'

(50) Latin Name: *Rosa hybrida*
Varietal Denomination: Poulcs017

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 41 days.

(21) Appl. No.: 10/812,762

(22) Filed: Mar. 29, 2004

(51) Int. Cl.[7] ..... A01H 5/00
(52) U.S. Cl. ..... Plt./103
(58) Field of Search ..... Plt./103

*Primary Examiner*—Kent Bell

(57) ABSTRACT

A new garden rose plant of the floribunda class which has abundant, white flowers and attractive foliage. This new and distinct variety has shown to be uniform and stable in the resulting generations from asexual propagation.

2 Drawing Sheets

Botanical classification: *Rosa hybrida.*
Variety denomination: 'Poulcs017'.

SUMMARY OF THE INVENTION

The present invention constitutes a new and distinct variety of garden rose plant which originated from a controlled crossing between the female seed parent, a rose plant named 'Bernina', a non-patented variety, and the male parent, an un-named seedling. The two parents were crossed during the summer of 1993 and the resulting seeds were planted in a controlled environment in Fredensborg, Denmark. The new variety is named 'Poulcs017'.

The new variety may be distinguished from its seed parent 'Bernina' by the following combination of characteristics:

1. 'Poulcs017' has a taller growth habit than 'Bernina'.
2. The seed parent is a recurrent bloomer while 'Poulcs017' blooms continuously.

The new variety may be distinguished from its pollen parent, an un-named seedling, by the following combination of characteristics:

1. While the pollen parent has creamy white flowers, 'Poulcs017' has flowers which are more pure white.
2. The pollen parent has a taller growth habit than 'Poulcs017'.

The objective of the hybridization of this rose variety was to create a new and distinct variety for garden use with unique qualities, such as:

1. Uniform and abundant pure flowers;
2. Vigorous, but compact growth when propagated both as a budded rose and on its own roots;
3. Disease resistance;
4. Suitability for production in containers.

This combination of qualities is not present in previously available commercial cultivars of this type, known to the inventors, and distinguish 'Poulcs017' from all other varieties of which we are aware.

As part of their rose development program, L. Pernille Olesen and Mogens N. Olesen germinated the seeds from the aforementioned hybridization during winter of 1993 and conducted evaluations on the resulting seedlings in a controlled environment in Fredensborg, Denmark.

'Poulcs017' was selected in the spring 1994 by the inventors as a single plant from the progeny of the aforementioned hybridization.

Asexual reproduction of 'Poulcs017' by traditional budding and rooted cuttings was first done by L. Pernille and Mogens N. Olesen in their nursery in Fredensborg, Denmark in July, 1994. This initial and other subsequent asexual propagations conducted in controlled environments have demonstrated that the characteristics of 'Poulcs017' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poulcs017'. Specifically illustrated in SHEET 1:

FIG. 1.1; Open flower, stem showing cluster of open flowers, branching, and the attachment of leaves, buds, and peduncles;

FIG. 1.2; Flower bud closed, flower bud as sepals unfold, and partially open;

Specifically illustrated in SHEET 2:

FIG. 2.1; Juvenile shoot with leaves exhibiting anthocyanin, and mature leaf;

FIG. 2.2; Juvenile stem exhibiting thorns, mature stem exhibiting thorns;

FIG. 2.3; Sepal, peduncle, receptacle;

FIG. 2.4; Petals detached.

DETAILED DESCRIPTION OF THE VARIETY

The following is a description of 'Poulcs017', as observed in its growth in a field nursery in Jackson County, Oreg. Observed plants are 3 years of age. Plants were grown on *Rosa multiflora* understock. Color references are made using The Royal Horticultural Society (London, England) Colour Chart, 1995, except where common terms of color are used.

For a comparison, several physical characteristics of the rose variety 'Poulen001', a rose variety from the same inventors described and illustrated in U.S. Plant patent application Ser. No. 10/264,508 dated Oct. 4, 2002 (abandoned) are compared to 'Poulcs017' in Chart 1.

CHART 1

| | 'Poulcs017' | 'POULen001' |
|---|---|---|
| Color of outer petals upon opening: inner surface | Green-White Group 157A | Yellow-White Group 158D |
| Petalage | 25 petals | 65 to 70 petals |
| Bloom diameter | 38 mm to 40 mm | 65 to 70 mm |
| Color of basal petals spots, upon opening | no distinct coloration at the base of the petal | Green-Yellow Group 1D |

FLOWER AND FLOWER BUD

Blooming habit: Continuous.

Flower bud:

*Size.*—Upon opening, 25 mm in length from base of receptacle to end of bud. 13 mm in diameter.

*Bud form.*—Pointed ovoid with slightly broadened base.

*Bud color.*—As sepals unfold, petals are Yellow Group 4D to Yellow-Green Group 150D. At ¼ opening petals are Yellow Group 4D.

*Sepals.*—Upper Surface: Color: Yellow-Green Group 144B. Lower Surface: Color: Yellow-Green Group 144A. Anthocyanic pigments the color of Brown Group 200A, occurring in well defined area at sepal apex. Texture: Moderately pubescent with a medium quantity of stipitate glands. Sepal Shape: Sepal apex is cirrhose. Base is flat at union with receptacle. Sepal Margin: Margins have medium foliaceous appendages on three of the five sepals. Size: 37 mm (l)×11 mm (w).

*Receptacle.*—Surface: Glabrous and smooth. Shape: Urn-shaped. Size: 8 mm (h)×6 mm (w). Color: Yellow-Green Group 145A. Anthocyanic pigments the color of Greyed-Red Group 178C observed.

*Peduncle.*—Surface: Smooth with stipitate glands. Length: 25 to 30 mm. Color: Yellow-Green Group 145A. Strength: Strong.

*Borne.*—In clusters of 3 to 7 flower buds per stem.

Flower bloom:

*Fragrance.*—Light floral scent.

*Duration.*—The blooms have a duration on the plant of approximately 10 to 14 days. After flowers have fully matured, petals fall cleanly away from plant.

*Size.*—On average, flower diameter is 38 mm to 40 mm when open. Flower depth is 23 mm.

*Form.*—Generally flowers have high pointed centers that are slightly open. Shape of flower when viewed from the side: Upon opening, upper part: Flat. Upon opening, lower part: Flat. Open flower, upper part: Flat. Open flower, lower part: Concave.

Petalage: On average 25 petals under normal conditions with 4 petaloids.

Color:

Upon opening, petals:

*Outermost petals.*—Outer side: Green-White Group 157D. Inner side: Green-White Group 157A.

*Innermost petals.*—Outer side: Green-White Group 157D. Inner side: Green-White Group 157A.

Upon opening, basal petal spots: No distinctive coloration at the petal base observed.

After opening, petals:

*Outermost petals.*—Outer side: Green-White Group 157D. Inner side: Green-White Group 157A.

*Innermost petals.*—Outer side: Green-White Group 157D. Inner side: Green-White Group 157A.

After opening, basal petal spots: No distinctive coloration at the petal base observed.

General tonality: On open flower Green-White Group 157D with intonations of Yellow-Green Group 149D. No change in the general tonality at the end of the $10^{th}$ day.

Petals:

*Petal reflex.*—Somewhat reflexed.

*Margin.*—Entire and uniform. Weak undulations of margin observed.

*Shape.*—Apex: Round. Base: Acute.

*Size.*—40 mm (l)×40 mm (w).

*Texture.*—Smooth.

*Thickness.*—Thick.

*Arrangement.*—Formal.

Petaloids:

*Quantity.*—4 to 7.

*Color.*—Upper Surface: Green-White Group 157A. Lower Surface: Green-White Group 157D.

*Size.*—30 mm (l)×30 mm (w).

*Shape.*—Apex: Round. Base: Acute.

Reproductive organs:

*Pistils.*—Length: 7 mm. Quantity: 37 (actual count).

*Pollen.*—None observed.

*Anthers.*—Size: 2 mm in length. Color: Yellow-Orange Group 167D. Quantity: 88 (actual count).

*Filaments.*—Color: Yellow-Green Group 150D. Length: 9 mm.

*Stigmas.*—Inferior relative to the length of the filaments and the height of the anthers. Color: Yellow-Green Group 150D.

*Styles.*—Color: Yellow-Green Group 150D.

*Hips.*—None Observed in the field nursery in Jackson County, Oreg.

PLANT

Plant growth: Moderate, upright to bushy. When grown as a budded field grown plant on *Rosa multiflora* understock, the average height of the plant is 90 cm and the average width is 65 cm.

Stems:

*Color.*—Young wood: Yellow-Green Group 144A. Older wood: Yellow-Green Group 144A.

*Surface texture.*—Young wood: Smooth. Older wood: Smooth.

Thorns:

*Incidence.*—3 thorns per 10 cm of stem.

*Size.*—8 mm in length.

*Color.*—Greyed-Red Group 181A.

*Shape.*—Deeply concave.

Plant foliage: Normal number of leaflets on normal leaves in middle of the stem: 5 leaflets.

*Compound leaf size.*—150 mm (l)×115 mm (w).

*Color.*—Mature Foliage: Upper surface is Green Group 137A. Lower surface is Yellow-Green Group 147B. Juvenile foliage: Upper surface is Yellow-Green Group 146A. Lower surface is Yellow-Green Group 147C.

Plant leaves and leaflets:

*Stipules.*—Size: 15 mm in length. Quantity: 2 per compound leaf. Shape: Linear with outward extending apecies. Margins: Finely serrated with average to above average amounts of stipitate glands. Color: Yellow-Green Group 146A.

*Petiole.*—Length: 25 mm. Color: Yellow-Green Group 144B. Underneath: Spines observed.

*Rachis.*—Length: 40 mm. Above: Color: Yellow-Green Group 144B. Observations: Stipitate glands. Underneath: Observations: Spines observed.

*Leaflet.*—Edge: Serrated. Size: 40 to 60 mm (l)×23 to 42 mm (w). Shape: Ovate. Base is: Rounded. Apex is: Acute to cuspidate. Texture: Smooth. Thickness: Thick. Arrangement: Odd pinnate. Venation: Reticulate. Glossiness: Moderately to slightly glossy.

Disease resistance: Above average resistance to mildew, rust, black spot, and *Botrytis* under normal growing conditions in Jackson County, Oreg.

Cold hardiness: The variety 'Poulcs017' has been found to be cold tolerant to USDA Cold Hardiness Zone 6.

It is claimed:

1. A new and distinct variety of rose plant of the floribunda rose class named 'Poulcs017', substantially as herein illustrated and described as a distinct and novel rose variety due to its abundant white flowers, disease resistance, and extended period of bloom.

* * * * *

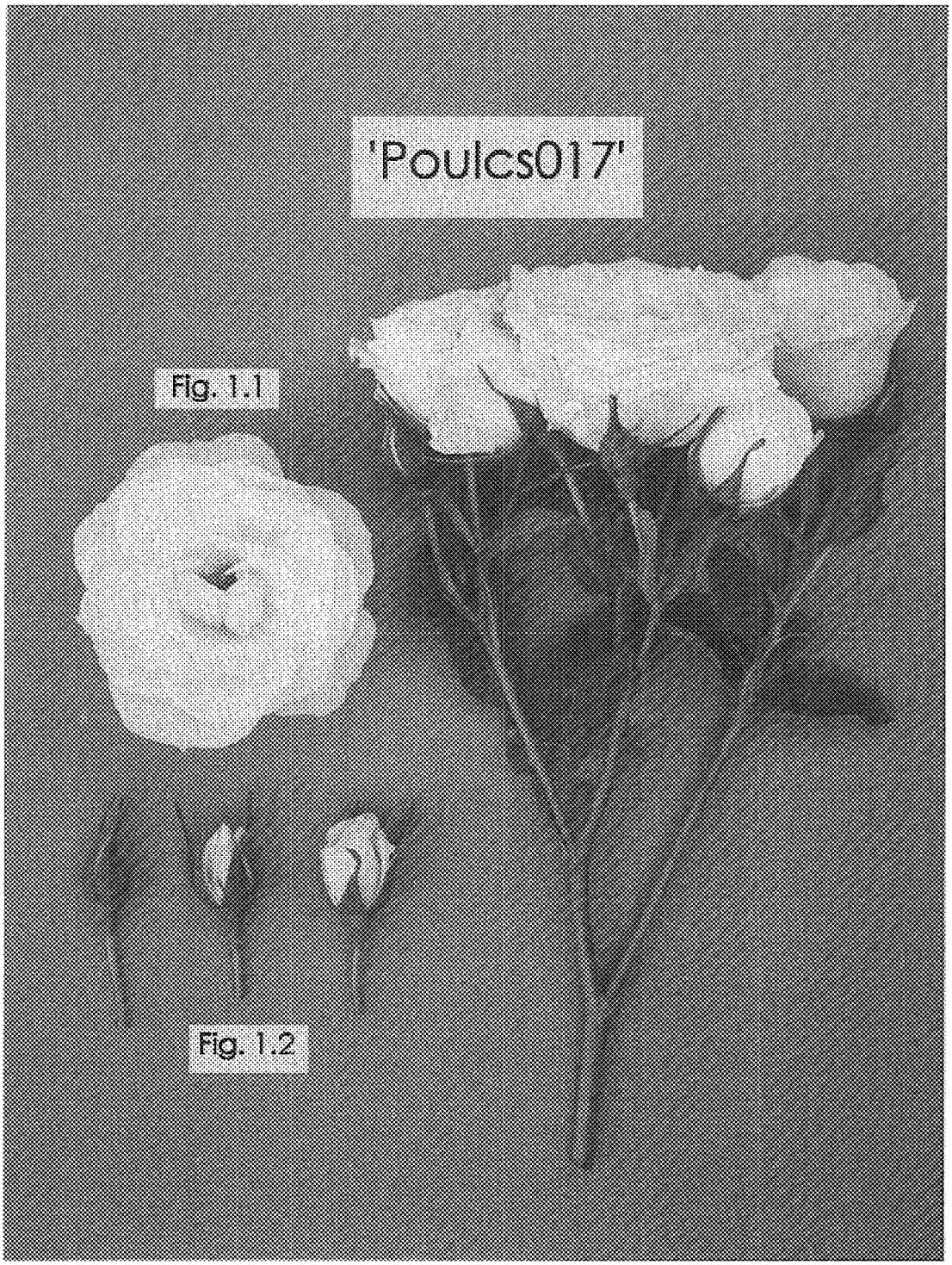
'Poulcs017'
Fig. 1.1
Fig. 1.2

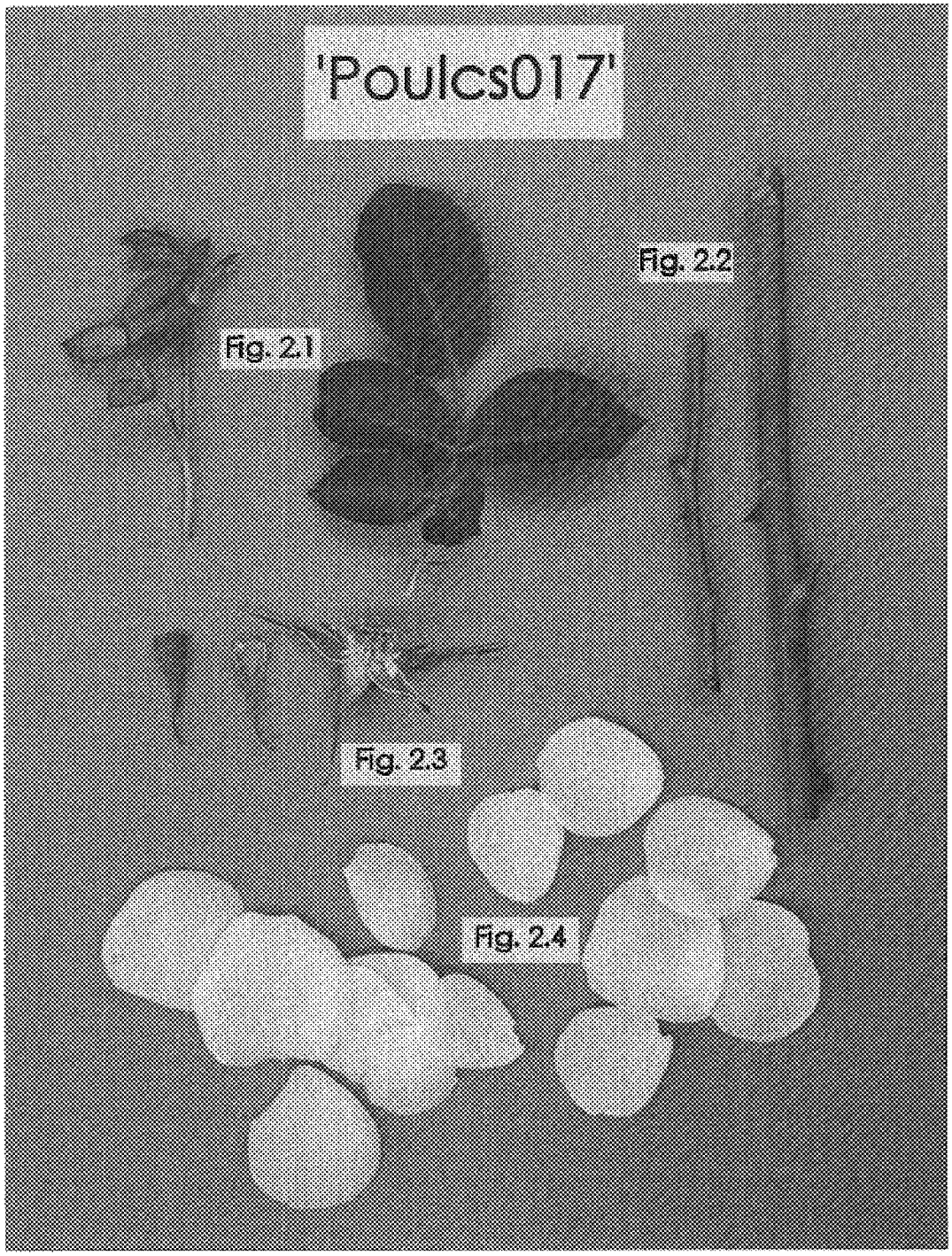
'Poulcs017'
Fig. 2.1
Fig. 2.2
Fig. 2.3
Fig. 2.4